US009695377B2

(12) United States Patent
Eveland et al.

(10) Patent No.: US 9,695,377 B2
(45) Date of Patent: Jul. 4, 2017

(54) PYRAN DISPERSANTS

(71) Applicant: The Lubrizol Corporation, Wickliffe, OH (US)

(72) Inventors: Renee A. Eveland, Kirkland, OH (US); Matthew D. Gieselman, Wickliffe, OH (US); Adam J. Preston, Mentor, OH (US); Joanne L. Jones, Nottingham (GB)

(73) Assignee: The Lubrizol Corporation, Wickliffe, OH (US)

( * ) Notice: Subject to any disclaimer, the term of this patent is extended or adjusted under 35 U.S.C. 154(b) by 25 days.

(21) Appl. No.: 14/648,105

(22) PCT Filed: Nov. 21, 2013

(86) PCT No.: PCT/US2013/071121
§ 371 (c)(1),
(2) Date: May 28, 2015

(87) PCT Pub. No.: WO2014/088814
PCT Pub. Date: Jun. 12, 2014

(65) Prior Publication Data
US 2015/0307804 A1    Oct. 29, 2015

Related U.S. Application Data

(60) Provisional application No. 61/734,431, filed on Dec. 7, 2012.

(51) Int. Cl.
| | |
|---|---|
| *C10M 129/20* | (2006.01) |
| *C07D 309/18* | (2006.01) |
| *C10M 157/04* | (2006.01) |
| *C10M 159/12* | (2006.01) |
| *C10M 129/86* | (2006.01) |
| *C07D 309/04* | (2006.01) |
| *C08F 110/10* | (2006.01) |

(52) U.S. Cl.
CPC ......... *C10M 157/04* (2013.01); *C07D 309/04* (2013.01); *C07D 309/18* (2013.01); *C08F 110/10* (2013.01); *C10M 129/20* (2013.01); *C10M 129/86* (2013.01); *C10M 159/12* (2013.01); *C10M 2205/026* (2013.01); *C10M 2207/044* (2013.01); *C10M 2207/08* (2013.01); *C10M 2215/28* (2013.01); *C10M 2217/043* (2013.01); *C10N 2230/04* (2013.01); *C10N 2230/36* (2013.01); *C10N 2230/40* (2013.01); *C10N 2230/42* (2013.01); *C10N 2230/43* (2013.01); *C10N 2230/45* (2013.01); *C10N 2240/10* (2013.01); *C10N 2240/103* (2013.01)

(58) Field of Classification Search
CPC  C10M 157/04; C10M 159/12; C10M 129/86; C10M 129/20; C10M 2215/28; C10M 2217/043; C10M 2205/026; C10M 2207/044; C10M 2207/08; C07D 309/04; C08F 110/10; C10N 2230/40; C10N 2230/45; C10N 2230/42; C10N 2230/43; C10N 2230/36; C10N 2240/10; C10N 2240/103; C10N 2230/04
See application file for complete search history.

(56) References Cited

U.S. PATENT DOCUMENTS

| | | |
|---|---|---|
| 3,248,327 A | 4/1966 | Whitaker |
| 3,846,319 A | 11/1974 | Hotten |
| 3,897,456 A | 7/1975 | Brewster |
| 2002/0134005 A1 | 9/2002 | Podlipskiy |
| 2008/0032914 A1 | 2/2008 | Mane et al. |

FOREIGN PATENT DOCUMENTS

| | | | | |
|---|---|---|---|---|
| DE | WO 2006125550 A1 | * | 11/2006 | ........... C07D 309/04 |
| EP | 2050743 A1 | | 4/2009 | |
| EP | 2161324 A1 | | 3/2010 | |

OTHER PUBLICATIONS

Metzger, J O, et al., "Aluminumchloride-Induced Additions of Formaldehyde to Alkenes", Bulletin des Societes Chimiques Beiges, 1994, pp. 393-397, vol. 103, No. 7-8, Louvain [U.A.] Centerick, BE.

* cited by examiner

*Primary Examiner* — Taiwo Oladapo
(74) *Attorney, Agent, or Firm* — Christopher P. Demas; Teresan W. Gilbert

(57) ABSTRACT

The disclosed technology relates to ashless compounds exhibiting neutral pH and having sufficient polarity to act as a dispersant. The disclosed technology additionally relates to the use of the ashless compounds in engine lubricants as dispersants for preventing engine deposit without degrading seals or increasing (i.e. contributing to) corrosion.

16 Claims, No Drawings

PYRAN DISPERSANTS

CROSS REFERENCE TO RELATED APPLICATION

This application claims priority from PCT Application Serial No. PCT/US2013/071121 filed on Nov. 21, 2013, which claims the benefit of U.S. Provisional Application No. 61/734,431 filed on Dec. 7, 2012.

BACKGROUND OF THE INVENTION

The disclosed technology relates to non-basic ashless compounds having sufficient polarity to act as dispersants. The disclosed technology additionally relates to the use of the ashless compounds in engine lubricants as dispersants for preventing engine deposits without degrading seals or increasing (i.e. contributing to) corrosion of yellow metals.

Detergent or dispersant compounds, depending on the compound's constitution, may upon combustion yield a non-volatile material such as, for example, boric oxide or phosphorus pentoxide. However, ashless detergents and dispersants do not ordinarily contain metal and therefore do not yield a metal-containing ash on combustion. Many types of ashless dispersants are known in the art.

(1) "Carboxylic dispersants" are reaction products of carboxylic acylating agents (acids, anhydrides, esters, etc.) reacted with nitrogen containing compounds (such as amines), organic hydroxy compounds (such as aliphatic compounds including monohydric and polyhydric alcohols, or aromatic compounds including phenols and naphthols and aromatic amines), and/or basic inorganic materials. These reaction products include imide, amide, and ester reaction products of carboxylic ester dispersants. Examples of these "carboxylic dispersants" are described in British Patent 1,306,529 and in many U.S. Patents including the following: U.S. Pat. Nos. 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, and Re. 26,433.

(2) "Amine dispersants" are reaction products of relatively high molecular weight aliphatic halides and amines, preferably polyalkylene polyamines. Examples thereof are described, for example, in the following U.S. Pat. Nos. 3,275,554, 3,438,757, 3,454,555, and U.S. Pat. No. 3,565,804.

(3) "Mannich dispersants" are the reaction products of alkyl phenols with aldehydes (especially formaldehyde) and amines (especially polyalkylene polyamines). The materials described in the following U.S. Patents are illustrative: U.S. Pat. Nos. 3,036,003, 3,236,770, 3,414,347, 3,448,047, 3,461,172, 3,539,633, 3,586,629, 3,591,598, 3,634,515, 3,725,480, 3,726,882, and U.S. Pat. No. 3,980,569.

(4) Post-treated dispersants are obtained by reacting a carboxylic, amine or Mannich dispersant with reagents such as dimercaptothiadiazoles, urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos. 3,200,107, 3,282,955, 3,367,943, 3,513,093, 3,639, 242, 3,649,659, 3,442,808, 3,455,832, 3,579,450, 3,600,372, 3,702,757, and 3,708,422.

(5) Polymeric dispersants are interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. Examples of polymeric dispersants thereof are disclosed in the following U.S. Pat. Nos. 3,329,658, 3,449,250, 3,519, 656, 3,666,730, 3,687,849, and 3,702,300.

The above-noted patents are incorporated by reference herein for their disclosures of ashless dispersants.

Ashless dispersants are important additives in engine lubricants for various purposes. One function of dispersants in engine lubricants is to maintain solid particles in suspension, thereby controlling undesirable engine deposits. However, the higher the treat rate of a dispersant in an engine oil, the more likely the dispersant will cause degradation of engine seals and corrosion. Thus, there is a need for an ashless compound that provides sufficient polarity to act as a dispersant, but does not induce seal degradation or corrosion.

SUMMARY OF THE INVENTION

The inventors have created new non-basic ashless compounds with sufficient polarity to act as dispersants.

One aspect of the invention relates to ashless compounds comprising the reaction product of a long chain hydrocarbyl group, preferably a long chain ethylenically unsaturated hydrocarbyl group, such as, for example, a polyolefin, such as poly(isobutylene) ("PIB"), with an aldehyde, such as, for example, formaldehyde or a derivative or reactive equivalent thereof, or ketone.

In one embodiment, the reaction to produce the reaction product can comprise at least one of an acid-catalyzed Alder-ene reaction or Prins reaction.

In an embodiment, the ashless compound reaction product can be a hydrocarbyl-substituted cyclic ether compound. The hydrocarbyl-substituted cyclic ether compound can comprise a cyclic ether consisting of a ring of 5 carbon atoms and 1 oxygen atom. The cyclic ether can have zero or one internal ethylenic double bond. At least one of the 5 carbon atoms of the cyclic ether can be substituted with a long chain hydrocarbyl, such as, for example, a polyolefin, including PIB. Likewise, one of the 5 carbon atoms of the cyclic ether can be substituted with a short chain hydrocarbyl group of from 1 to about 10 carbon atoms, or the requisite number of hydrogens to complete the valence at the substituted carbon atom. Preferably, the long chain hydrocarbyl, e.g., polyolefin/PIB, substitution is at least one carbon atom separated on the cyclic ether from the oxygen atom of the cyclic ether.

In one embodiment, the hydrocarbyl-substituted cyclic ether compound can be a polyolefin substituted dihydropyran.

In another embodiment, the hydrocarbyl-substituted cyclic ether compound can be a polyolefin substituted tetrahydropyran.

In a further embodiment, the hydrocarbyl-substituted cyclic ether compound can comprise a compound of formula 1:

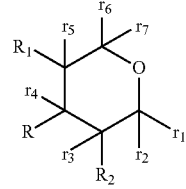

Formula 1 where:

R, $R_1$, and $R_2$, independently, can be at least one of (1) a long chain hydrocarbyl group, or (2) H, $r_1$ to $r_7$, independently, can be at least one of (1) H, (2) a short chain hydrocarbyl group, (3) an internal ethylenic double bond formed from the interaction with an "r" from a neighboring carbon atom on the cyclic ether ring, and (4) absent in contribution to an external ethylenic double bond formed from the interaction with an "r" or "R" substituent of the same carbon atom on the cyclic ether ring.

One embodiment of the hydrocarbyl-substituted cyclic ether compound can be the compound of formula 1 wherein R is a PIB of 140 to about 5000 Mn, $R_1$, $R_2$ and each of $r_1$ to $r_3$, $r_6$ and $r_7$ are H, and $r_4$ and $r_5$ interact to form an internal ethylenic double bond.

To the inventors' surprise, the hydrocarbyl-substituted cyclic ether compounds disclosed herein contribute to improving the cleanliness of an engine lubricant. In addition, the hydrocarbyl-substituted cyclic ether compounds disclosed herein do not effect engine seals or cause corrosion.

Thus, another aspect of the invention is a composition comprising (A) an oil of lubricating viscosity, and (B) any of the above embodiments of the hydrocarbyl-substituted cyclic ether compound.

In an embodiment, the composition can optionally comprise (C) a dispersant comprising at least one of a carboxylic, amine, Mannich, post-treated, or polymeric dispersant. Preferably the dispersant is a carboxylic dispersant, and most preferably a PIB-succinimide. In one embodiment, the composition can comprise a carboxylic dispersant from about 0.01 to about 20 wt. % on an active basis.

In a still further embodiment, the invention is directed to a method of operating an engine comprising (1) supplying to the engine a composition comprising (A) an oil of lubricating viscosity, (B) a hydrocarbyl-substituted cyclic ether compound as described herein, and optionally (C) at least one of a carboxylic, amine, Mannich, post-treated, or polymeric dispersant, and (2) operating the engine.

DETAILED DESCRIPTION OF THE INVENTION

Various preferred features and embodiments will be described below by way of non-limiting illustration.

In one embodiment the invention is directed to ashless compounds comprising the reaction products of a long chain hydrocarbyl group with an aldehyde or ketone.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include: hydrocarbon substituents, including aliphatic, alicyclic, and aromatic substituents; substituted hydrocarbon substituents, that is, substituents containing non-hydrocarbon groups which, in the context of this invention, do not alter the predominantly hydrocarbon nature of the substituent or its functionality; and hetero substituents, that is, substituents which similarly have a predominantly hydrocarbon character but contain other than carbon in a ring or chain. A more detailed definition of the term "hydrocarbyl substituent" or "hydrocarbyl group" is found in paragraphs [0137] to of published application US 2010-0197536.

The long chain hydrocarbyl group of the reaction product can contain from about 10 to about 600 carbon atoms, alternately from about 25 to about 500 carbon atoms, or in another alternative from about 50 to about 400 carbon atoms, or about 50 to about 200 carbon atoms. Preferably the long chain hydrocarbyl group can be linear or branched and consist of carbon and hydrogen atoms.

Preferably the long chain hydrocarbyl group is an ethylenically unsaturated hydrocarbyl group. The hydrocarbyl group may have a high methylvinylidene isomer content. These include the hydrocarbyl groups wherein at least about 50% by weight, and in one embodiment at least about 70% by weight, of the hydrocarbyl groups have methylvinylidene end groups.

Preferably the long chain hydrocarbyl group can be a polyolefin. The polyolefin employed to produce the reaction product may be a homopolymer, copolymer, or interpolymer. The polyolefin may be prepared from polymerisable monomers containing about 2 to about 16, or about 2 to about 8, or about 2 to about 6 carbon atoms. Often the polymerisable monomers comprise one or more of ethylene, propylene, isobutene, 1-butene, isoprene, 1,3-butadiene, decene or mixtures thereof.

The polyolefin may be a "conventional" polyolefin or a "high vinylidene" polyolefin, and preferably "high vinylidene." The difference between a conventional polyolefin and a high vinylidene polyolefin can be illustrated by reference to the production of poly(isobutylene) ("PIB"). In a process for producing conventional PIB (a), isobutylene is polymerized in the presence of $AlCl_3$ to produce a mixture of polymers comprising predominantly trisubstituted olefin (III) and tetrasubstituted olefin (IV) end groups, with only a very small amount (for instance, less than 20 percent) of chains containing a terminal vinylidene group (I). In an alternative process, (b), isobutylene is polymerized in the presence of $BF_3$ catalyst to produce a mixture of polymers comprising predominantly (for instance, at least 70 percent) terminal vinylidene groups, with smaller amounts of tetrasubstituted end groups and other structures. The materials produced in the alternative method, sometimes referred to as "high vinylidene PIB," are also described in U.S. Pat. No. 6,165,235, Table 1.

| PIB Terminal Groups | Percent in Conventional PIB | Percent in High Vinylidene PIB |
|---|---|---|
| $CH_3$—$\underset{\underset{CH_3}{\|}}{\overset{\overset{CH_3}{\|}}{C}}$—$CH_2$—$\overset{\overset{CH_3}{\|}}{C}$=$CH_2$ <br> I | 4-5% | 50-90% |
| $\underset{\underset{CH_3}{\|}}{\overset{\overset{CH_3}{\|}}{C}}$—CH=$C\overset{CH_3}{\underset{CH_3}{<}}$ <br> II | 0-2% | 6-35% |
| —$CH_2$—$\overset{\overset{CH_3}{\|}}{C}$=CH—$CH_3$ <br> III | 63-67% tri-substituted | 50-90% |
| —CH—$\overset{\overset{CH_3}{\|}}{C}$=$C\overset{CH_3}{\underset{CH_3}{<}}$ with $CH_3$ <br> IV | 22-28% tetrasubstituted IV and IVa | 1-15% |

-continued

| PIB Terminal Groups | Percent in Conventional PIB | Percent in High Vinylidene PIB |
|---|---|---|
| $$\mathrm{-\underset{\underset{IVA}{|}}{C}=\underset{\underset{}{|}}{C}-\underset{\underset{CH_3}{|}}{C}\diagup \begin{array}{c}CH_3\\ \\ CH_3\end{array}}$$ with CH₃, CH₃ groups | | |
| $$\mathrm{-CH_2-\underset{\underset{V}{\|}}{\overset{\overset{CH_2}{\|}}{C}}-CH_2-CH_3}$$ | 5-8% | 0-4% |
| OTHER | 0-10% | |

Typical examples of a polyolefin include PIB; polypropylene; polyethylene; a copolymer derived from isobutene and butadiene; a copolymer derived from isobutene and isoprene; or mixtures thereof. Useful polyolefins include PIBs having a number average molecular weight of 140 to 5000, in another instance of 400 to 2500, and in a further instance of 140 or 500 to 1500. The PIB may have a vinylidene double bond content of 5 to 69%, in a second instance of 50 to 69%, and in a third instance of 50 to 95%.

In the formation of the reaction product, the conditions for the reaction of the long chain hydrocarbyl group with the aldehyde or ketone, and the relative concentrations of such components, should preferably be sufficient that a majority of the long chain hydrocarbyl group has reacted with at least one molecule of the aldehyde or ketone. That is, it is preferred, for optimum performance of the dispersant, that no more than 30 percent by weight polyisobutene or other long chain hydrocarbyl group should remain unreacted in the resulting dispersant. Preferably no more than 25 percent unreacted long chain hydrocarbyl group should remain, and more preferably no more than 20 percent. Determination of conditions to assure a sufficient degree of reaction is within the abilities of the person skilled in the art.

The aldehyde or ketone reactant used to prepare the reaction product is a carbonyl compound other than a carboxy-substituted carbonyl compound (i.e. a non-carboxy-substituted carbonyl compound). Suitable compounds include those having the general formula RC(O)R', wherein R and R' are each, independently, H or a hydrocarbyl group of about one to about 10 carbon atoms, preferably two to about four. As noted in the description, hydrocarbyl groups may contain other groups or heteroatoms which do not interfere with the process and products of this invention. Preferably, the aldehyde or ketone contains from 1 to about 12 carbon atoms.

The aldehyde used to form the reaction product can have 1 to 10, or 1 to 8, or 1 to 6 carbon atoms. Suitable aldehydes include formaldehyde, acetaldehyde, propionaldehyde, butyraldehyde, isobutyraldehyde, pentanal, hexanal, heptaldehyde, octanal, benzaldehyde, and higher aldehydes. Other aldehydes, such as dialdehydes, especially glyoxal, are useful, although monoaldehydes are generally preferred. In one embodiment, the non-carboxy-substituted carbonyl compound is a hydrocarbyl substituted aldehyde, preferably a hydrocarbyl substituted mono-aldehyde.

The most preferred aldehyde is formaldehyde, which can be supplied as the aqueous solution often referred to as formalin, but is more often used in the polymeric form as paraformaldehyde, which is a reactive equivalent of, or a source of, formaldehyde. Other reactive equivalents include hydrates or cyclic trimers. In one embodiment, the aldehyde employed to form the reaction product consists of a mono-aldehyde, such as formaldehyde.

Suitable ketones include acetone, butanone, methyl ethyl ketone, and other ketones. Preferably, one of the hydrocarbyl groups is methyl.

Mixtures of two or more aldehydes and/or ketones are also useful. In one embodiment, the reaction consists of a long chain hydrocarbyl group, e.g., PIB, and an aldehyde, preferably a mono-aldehyde, or a ketone.

The reaction in the preparation of the reaction product involves the acid catalyzed addition of one or more equivalents of the aldehyde or ketone to the polyolefin. The reaction may occur through either two contiguous Alder-ene reactions followed by an acid mediated ring closure, or by Prins chemistry. In one embodiment, the reaction (e.g., Alder-ene or Prins reaction) can proceed in the absence of water. In another embodiment, the reaction can proceed under dry conditions employing a solid aldehyde, such as solid formaldehyde (i.e., paraformaldehyde).

In one embodiment, the reaction product comprises a hydrocarbyl-substituted cyclic ether compound. The hydrocarbyl-substituted cyclic ether compound can comprise a cyclic ether consisting of a ring of 5 carbon atoms and 1 oxygen atom. The ring of the cyclic ether can contain zero internal ethylenic double bonds, or one internal ethylenic double bond. In addition, at least one of the 5 carbon atoms of the cyclic ether ring can be substituted with (1) the long chain hydrocarbyl group, such as a polyolefin as described above, (2) a short chain hydrocarbyl group, or (3) the requisite number of hydrogens to complete the valence at the substituted carbon.

The long chain hydrocarbyl group may be a polyolefin as described above. When the cyclic ether ring is substituted by a long chain hydrocarbyl, e.g., a polyolefin, the long chain hydrocarbyl group will bond to a carbon atom at least one carbon atom separated from the oxygen atom of the cyclic ether ring.

The short chain hydrocarbyl group can bond to any one of the 5 carbon atoms of the cyclic ether ring. The short chain hydrocarbyl group preferably comprises from 1 to about 10 carbon atoms, alternately 1 to about 8 carbon atoms, or, as a further alternate, 1 to about 6 carbon atoms. The short chain hydrocarbyl group preferably is linear or branched but may also comprise aryl groups. Preferably, the short chain hydrocarbyl group consists of carbon and hydrogen atoms, but it may also comprise heteroatoms, such as, for example, nitrogen, oxygen and sulfur. Heteroatoms may be present particularly as a part of a heteroaryl group. The short chain hydrocarbyl group can be hydrogenated, e.g., methyl, or can comprise an ethylenic double bond, e.g., methylene.

The requisite number of hydrogens to complete the valence at a carbon atom will be well known to one of ordinary skill in the art, taking into account the hydrocarbyl substituents and any internal ethylenic double bond associated with the particular carbon atom in question.

In one embodiment, the hydrocarbyl-substituted cyclic ether compound can be illustrated by a compound of formula 1:

Formula 1

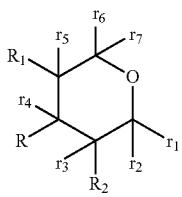

where:

R, $R_1$, and $R_2$, independently, can be at least one of (1) a long chain hydrocarbyl group, as defined above, preferably a polyolefin, as defined above, most preferably a PIB, as defined above and having a number average molecular weight of 140 to 5000, in another instance of 400 to 2500, and in a further instance of 140 or 500 to 1500, or (2) H, $r_1$ to $r_7$, independently, can be at least one of (1) H, (2) a short chain hydrocarbyl group as defined above, (3) an internal ethylenic double bond formed from the interaction with an r from a neighboring carbon atom on the cyclic ether ring, and (4) absent in contribution to an external ethylenic double bond formed from the interaction with an r or R substituent of the same cyclic ether ring carbon atom.

In a preferred embodiment, formula 1 can be a polyolefin substituted dihydropyran, represented, for example, by formula 1(a), where R is a PIB of 140 to about 5000 Mn, or as more specifically defined above, $R_1$, $R_2$ and each of $r_1$ to $r_3$, $r_6$ and $r_7$ are H, and $r_4$ and $r_5$ interact to form an internal ethylenic double bond.

formula 1(a)

In another preferred embodiment, formula 1 can be a polyolefin substituted tetrahydropyran, represented, for example, by formula 1(b), where R is a PIB of 140 to about 5000 Mn, or as more specifically defined above, $r_4$ contributes to an external double bond, and each of $R_1$, $R_2$, and $r_1$ to $r_3$, and $r_5$ to $r_7$ are H.

formula 1(b)

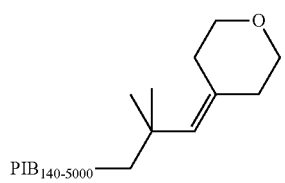

In another alternate embodiment, formula 1 can be a polyolefin substituted tetrahydropyran, represented, for example, by formula 1(c), where $R_1$ is a PIB of 140 to about 5000 Mn, or as more specifically defined above, R and $r_4$ interact to form a short chain hydrocarbyl group of 1 carbon atom having an ethylenic double bond, i.e. methylene, and each of $R_2$, $r_1$ to $r_3$, and $r_5$ to $r_7$ are H.

formula 1(c)

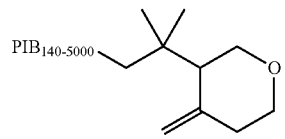

One aspect of the invention is an engine lubricant comprising (A) an oil of lubricating viscosity, and (B) the ashless compounds, i.e. hydrocarbyl-substituted cyclic ether compounds, described above.

In one embodiment, the ashless compounds of (B) described herein may be added to an oil of lubricating viscosity of (A) in a range of 0.01 wt % to 20 wt %, or 0.05 wt % to 10 wt %, or 0.08 wt % to 5 wt %, or 0.1 wt % to 3 wt % of the lubricating composition, on an active basis.

The oils of lubricating viscosity of (A) can include, for example, natural and synthetic oils, oil derived from hydrocracking, hydrogenation, and hydrofinishing, unrefined, refined and re-refined oils and mixtures thereof. Oils of lubricating viscosity may also be defined as specified in the American Petroleum Institute (API) Base Oil Interchangeability Guidelines.

A more thorough elaboration of the various oils that can be employed in the present invention can be found in paragraphs [0104] to [0111] of U.S. Publication #2011/0306528, to Gieselman et al., published Dec. 15, 2011.

The lubricant composition may be in the form of a concentrate and/or a fully formulated lubricant. If the ashless dispersant of the present invention is in the form of a concentrate (which may be combined with additional oil to form, in whole or in part, a finished lubricant), the ratio of the ashless dispersant to the oil of lubricating viscosity and/or to diluent oil include the ranges of 1:99 to 99:1 by weight, or 80:20 to 10:90 by weight.

The composition can optionally comprise (C) a dispersant comprising at least one of a carboxylic, amine, Mannich, post-treated, and polymeric dispersant.

Dispersants are often known as ashless-type dispersants because, prior to mixing in a lubricating oil composition, they do not contain ash-forming metals and they do not normally contribute any ash forming metals when added to a lubricant and polymeric dispersants. Ashless type dispersants are characterized by a polar group attached to a relatively high molecular weight hydrocarbon chain. Typical ashless dispersants include carboxylic dispersants, such as, for example, N-substituted long chain alkenyl succinimides. Examples of N-substituted long chain alkenyl succinimides include PIB succinimide with number average molecular weight of the PIB substituent in the range 350 to 5000, or 500 to 3000. Succinimide dispersants and their preparation are disclosed, for instance in U.S. Pat. No. 4,234,435. Succinimide dispersants are typically the imide formed from a polyamine, typically a poly(ethyleneamine) or an aromatic polyamine, such as amino diphenylamine (ADPA).

In one embodiment, the lubricant composition can further comprise an amine dispersant, such as, for example, the reaction product of a PIB succinic anhydride and an amine, preferably a polyamine, and preferably an aliphatic polyamine, such as ethylene polyamine (i.e., a poly(ethyleneamine)), a propylene polyamine, a butylene polyamine, or a mixture of two or more thereof. The aliphatic polyamine may be ethylene polyamine. The aliphatic polyamine may be selected from ethylenediamine, diethylenetriamine, triethylenetetramine, tetraethylenepentamine, pentaethylenehexamine, polyamine still bottoms, or a mixture of two or more thereof.

In one embodiment the lubricant composition further comprises at least one PIB succinimide dispersant derived from PIB with number average molecular weight in the range 350 to 5000, or 500 to 3000. The PIB succinimide may be used alone or in combination with other dispersants.

Another class of ashless dispersant is Mannich bases. Mannich dispersants are the reaction products of alkyl phenols with aldehydes (especially formaldehyde) and amines (especially polyalkylene polyamines). The alkyl group typically contains at least 30 carbon atoms.

The dispersants may also be post-treated by conventional methods by a reaction with any of a variety of agents. Among these are boron, urea, thiourea, dimercaptothiadiazoles, carbon disulfide, aldehydes, ketones, carboxylic acids, hydrocarbon-substituted succinic anhydrides, maleic anhydride, nitriles, epoxides, phosphorus compounds and/or metal compounds.

The optional dispersant can also be a polymeric dispersant. Polymeric dispersants are interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates.

The optional dispersant of (C) may be present at 0 wt % to 20 wt %, or 0.1 wt % to 15 wt %, or 0.1 wt % to 10 wt %, or 1 wt % to 6 wt %, or 3 wt % to 12 wt % of the lubricating composition.

The engine lubricant may also contain conventional detergents (detergents prepared by processes known in the art). Most conventional detergents used in the field of engine lubrication obtain most or all of their basicity or TBN from the presence of basic metal-containing compounds (metal hydroxides, oxides, or carbonates, typically based on such metals as calcium, magnesium, zinc, or sodium). Such metallic overbased detergents, also referred to as overbased or superbased salts, are generally single phase, homogeneous Newtonian systems characterized by a metal content in excess of that which would be present for neutralization according to the stoichiometry of the metal and the particular acidic organic compound reacted with the metal. The overbased materials are typically prepared by reacting an acidic material (typically an inorganic acid or lower carboxylic acid such as carbon dioxide) with a mixture of an acidic organic compound (also referred to as a substrate), a stoichiometric excess of a metal base, typically in a reaction medium of an inert, organic solvent (e.g., mineral oil, naphtha, toluene, xylene) for the acidic organic substrate. Typically also a small amount of promoter such as a phenol or alcohol is present, and in some cases a small amount of water. The acidic organic substrate will normally have a sufficient number of carbon atoms to provide a degree of solubility in oil.

The overbased metal-containing detergent may be selected from the group consisting of non-sulfur containing phenates, sulfur containing phenates, sulfonates, salixarates, salicylates, and mixtures thereof, or borated equivalents thereof. The overbased detergent may be borated with a borating agent such as boric acid.

Overbased detergents are known in the art. In one embodiment the sulfonate detergent may be a predominantly linear alkylbenzene sulfonate detergent having a metal ratio of at least 8 as is described in paragraphs [0026] to [0037] of US Patent Application 2005-065045. The term "metal ratio" is the ratio of the total equivalents of the metal to the equivalents of the acidic organic compound. A neutral metal salt has a metal ratio of one. A salt having 4.5 times as much metal as present in a normal salt will have metal excess of 3.5 equivalents, or a ratio of 4.5.

In one embodiment the overbased metal-containing detergent is calcium or magnesium overbased detergent. In one embodiment, the lubricating composition comprises an overbased calcium sulfonate, an overbased calcium phenate, or mixtures thereof. The overbased detergent may comprise calcium sulfonate with a metal ratio of at least 3.

The overbased detergent of the invention may be present in an amount from 0.05% by weight to 5% by weight of the composition. In other embodiments the overbased detergent may be present from 0.1%, 0.3%, or 0.5% up to 3.2%, 1.7%, or 0.9% by weight of the lubricating composition. Similarly, the overbased detergent may be present in an amount suitable to provide from 1 TBN to 10 TBN to the lubricating composition. In other embodiments the overbased detergent is present in amount which provides from 1.5 TBN or 2 TBN up to 3 TBN, 5 TBN, or 7 TBN to the lubricating composition.

The engine lubricant may additionally comprise other performance additives as well. The other performance additives can comprise at least one of metal deactivators, viscosity modifiers, friction modifiers, antiwear agents, corrosion inhibitors, dispersant viscosity modifiers, extreme pressure agents, antiscuffing agents, antioxidants, foam inhibitors, demulsifiers, pour point depressants, seal swelling agents and mixtures thereof. Typically, fully-formulated lubricating oil will contain one or more of these performance additives.

The total combined amount of the optional performance additives present in one embodiment can be from 0 or 0.01 wt. % to 50 wt. %, in another embodiment 0 or 0.01 to 40 wt. %, in another embodiment 0 or 0.01 to 30 wt. % and in another embodiment 0.05 or 0.1 or 0.5 to 20 wt. % of the lubricating composition. In one embodiment, the total combined amount of the additional performance additive compounds present on an oil free basis ranges from 0 wt % to 25 wt % or 0.01 wt % to 20 wt % of the composition. Although, one or more of the other performance additives may be present, it is common for the other performance additives to be present in different amounts relative to each other.

The lubricating composition may be utilized in an internal combustion engine. The internal combustion engine may or may not have an Exhaust Gas Recirculation system.

In one embodiment the internal combustion engine may be a diesel fuelled engine (typically a heavy duty diesel engine), a gasoline fuelled engine, a natural gas fuelled engine or a mixed gasoline/alcohol fuelled engine. In one embodiment the internal combustion engine may be a diesel fuelled engine and in another embodiment a gasoline fuelled engine. In one embodiment the engine may be a spark ignited engine and in one embodiment a compression engine.

The internal combustion engine may be a 2-stroke or 4-stroke engine. Suitable internal combustion engines include marine diesel engines, aviation piston engines, low-load diesel engines, and automobile and truck engines.

The lubricant composition for an internal combustion engine may be suitable for any engine lubricant irrespective of the sulfur, phosphorus or sulfated ash (ASTM D-874) content. The sulfur content of the engine oil lubricant may be 1 wt % or less, or 0.8 wt % or less, or 0.5 wt % or less, or 0.3 wt % or less. In one embodiment the sulfur content may be in the range of 0.001 wt % to 0.5 wt %, or 0.01 wt % to 0.3 wt %. The phosphorus content may be 0.2 wt % or less, or 0.1 wt % or less, or 0.085 wt % or less, or even 0.06 wt % or less, 0.055 wt % or less, or 0.05 wt % or less. In one embodiment the phosphorus content may be 100 ppm to 1000 ppm, or 325 ppm to 700 ppm. The total sulfated ash content may be 2 wt % or less, or 1.5 wt % or less, or 1.1 wt % or less, or 1 wt % or less, or 0.8 wt % or less, or 0.5 wt % or less. In one embodiment the sulfated ash content may be 0.05 wt % to 0.9 wt %, or 0.1 wt % to 0.2 wt % to 0.45 wt %.

In one embodiment the lubricating composition is an engine oil, wherein the lubricating composition is characterized as having at least one of (i) a sulfur content of 0.5 wt % or less, (ii) a phosphorus content of 0.1 wt % or less, and (iii) a sulfated ash content of 1.5 wt % or less.

In one embodiment the lubricating composition comprises less than 1.5% by weight unreacted polyisobutene, or less than 1.25%, or less than 1.0%.

The ashless dispersant compounds and the lubricating compositions containing the ashless dispersant compounds can be employed in a method of improving one of deposit performance, seal performance and corrosion performance in an engine by applying the ashless compounds or lubricating composition containing the ashless compounds to the engine and operating the engine.

In an embodiment, the ashless dispersant compounds do not contribute to total acid number (TAN) or total base number (TBN), i.e. the TAN and TBN of the compounds is zero or essentially zero (essentially meaning merely trace amounts associated, for example, with impurities, but not otherwise effective to bring TAN or TBN to the formulation). In another embodiment, the TAN is less than about 5, or in some embodiments 4 or even 3 or 2, and preferably less than 1. In another embodiment, the TBN is less than about 5, or in some embodiments 4 or even 3 or 2, and preferably less than 1.

An additional amount of a PIB Succinimide, such as the reaction product of a PIB succinic anhydride and an amine, preferably an aliphatic amine, and preferably an aliphatic polyamine, such as, for example, polyethylene polyamine (PEPA), may be employed in the method.

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

As used herein, the transitional phrases "comprising", "consisting essentially of" and "consisting of" define the scope of disclosure with respect to what un-recited additional components or steps, if any, are excluded from the scope of the disclosed embodiments. The transitional term "comprising", which is synonymous with "including," "containing," or "characterized by," is inclusive or open-ended and does not exclude additional, un-recited elements or method steps. In contrast, the transitional phrase "consisting of" excludes any element, step, or ingredient not specified in the disclosed embodiment. The transitional phrase "consisting essentially of" is intended to limit the scope of a disclosed embodiment to the specified materials or steps and those materials or steps that one of ordinary skill would understand not to materially affect the basic and novel characteristics of the disclosed embodiment. It is intended that the terms "consisting of" and "consisting essentially of" may be employed as alternative embodiments in place of "comprising" language in the above disclosure.

EXAMPLES

Sample 1: Reaction Product of a Long Chain Hydrocarbyl Group with an Aldehyde A 1 L four-necked flask is outfitted with a thermowell, overhead stirrer, nitrogen purge, heating mantle, and solid screw-thread addition funnel. 445 grams of a 1000 Mn high vinylidene PIB is charged to the flask and the assembly is purged with nitrogen (0.5 scfh). Methane sulfonic acid (0.6 g) is added and the mixture is heated to 115° C. with stirring. 30.1 grams of paraformaldehyde is added slowly via addition funnel over 3.5 h. The temperature is raised to 120° C. and the preparation is stirred for 4 h. The preparation is cooled to 90° C. and sodium hydroxide (50% in water, 0.5 g) is added. The temperature is increased to 130° C. and stirred for 1 h. The flask is cooled to 90° C. and diatomaceous earth is added. The product is filtered to yield 380 g.

Example 1

A comparison of the total acid number (TAN), total base number (TBN) and the retention factor (Rf-value, measure of polarity) of Sample 1 against a 1550 Mn Succinimide Dispersant (Succinimide) and a 1000 Mn PIB is provided in Table 1 below.

TABLE 1

Dispersant Comparisons

| Sample | TAN | TBN | Rf |
|---|---|---|---|
| Succinimide | 5 | 13 | 0.00 |
| PIB | 0 | 0 | 0.79 |
| Sample 1 | 0 | 0 | 0.35-0.63 |

Example 2

Four mid-SAPS oil (sulfated ash ceiling of 0.8%) formulations are prepared including a combination of Succinimide with Sample 1 top treated at 3% w/w. A Comparative Formulation with just Succinimide is also prepared. The formulations are tested according to the Volkswagen Viton™ Seal test PV3344. The PV-3344 test is an industry standard test designed to evaluate the effect of motor oils on Parker-Pradifa SRA AK6 (fluorocarbon) seal material. The test samples are measured for tensile strength, rupture elongation and cracking. The formulations (w/w basis) and seal results (final tensile strength and final rupture elongation strength) are shown in Table 2. Higher numbers indicate better seal performance.

TABLE 2

Comparative and Inventive Formulas.

| Description | Comparative Formulation 1 | Formulation 1 | Formulation 2 | Formulation 3 | Formulation 4 |
|---|---|---|---|---|---|
| Vis Grade | 5W-40 | 5W-40 | 5W-40 | 5W-40 | 5W-40 |
| DI contained | | | | | |
| Standard additive package | 4.55 | 4.55 | 4.55 | 4.55 | 4.55 |
| Detergent system | 1.3 | 1.3 | 1.3 | 1.3 | 1.3 |
| Succinimide | 5 | 5 | 4.3 | 3.6 | 2.8 |
| Sample 1 | — | 3 | 3 | 3 | 3 |
| Pour Point Depressant | 0.13 | 0.13 | 0.13 | 0.13 | 0.13 |
| Viscosity Modifier | 1.4 | 1.4 | 1.4 | 1.4 | 1.4 |
| Group III basestock | balance | balance | balance | balance | balance |
| PV3344 Seals | | | | | |
| Final Tensile Strength | 10 | 10 | 11 | 11 | 12 |
| Final rupture elongation | 183 | 195 | 217 | 221 | 235 |

Table 2 shows that as the standard Succinimide dispersant is reduced, seal performance improves. The data also shows that including the inventive dispersant did not affect the final tensile strength of the seals and actually improved rupture elongation.

Example 3

Formulation 1 is tested against the Comparative Formulation using the Volkswagen™ 1.6 L Diesel Intercooler test (Volkswagen™ VW TDI test). The TDI engine test is a turbo-charged direct injection fired engine test run under specified conditions for 54 h. At the end of the test, the pistons are visually rated for cleanliness on a scale of 0-100 with 100 indicating a piston clean and free of deposits. Table 3 shows the ratings for various parts of the piston including grooves 1-3 and the first and second land.

TABLE 3

VW TDi Performance of the Comparative and Inventive Lubricants.

| Rating Parameter | Comparative Formulation 1 | Formulation 1 |
|---|---|---|
| Groove 1 | 0 | 0 |
| Groove 2 | 57.2 | 87.24 |
| Groove 3 | 100 | 100 |
| Land 2 | 47.33 | 57.82 |
| Land 3 | 98.78 | 98.08 |
| Average Rating | 60.7 | 68.6 |

It is clear that groove 2 was greatly improved by the presence of the inventive dispersant of Sample 1 while land 2 was also directionally improved.

The most important rating is the weighted average piston rating. The presence of the inventive dispersant of Sample 1 boosted the average rating by almost 9 units. This is considered a large improvement in this test and is directly attributable to the presence of Sample 1.

Each of the documents referred to above is incorporated herein by reference. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. An ashless compound comprising the reaction product of a long chain ethylenically unsaturated hydrocarbyl group with a non-carboxy-substituted carbonyl compound selected from an aldehyde and a ketone, wherein the compound is a polyolefin substituted dihydropyran.

2. The compound of claim 1, wherein said long chain ethylenically unsaturated hydrocarbyl group comprises from about 10 to about 600 carbon atoms.

3. The compound of claim 1, wherein said long chain ethylenically unsaturated hydrocarbyl group is a polyolefin of number average molecular weight of from about 140 to 5000.

4. The compound of claim 1, wherein said non-carboxy-substituted carbonyl compound is a hydrocarbyl substituted mono-aldehyde.

5. The compound of claim 1, wherein said aldehyde is formaldehyde or a derivative or reactive equivalent thereof.

6. The compound of claim 1, wherein said reaction comprises at least one of an acid-catalyzed Alder-ene reaction or Prins reaction.

7. The compound of claim 6, wherein said reaction is performed in the absence of water.

8. The compound of claim 1, wherein the reaction product comprises a cyclic ether consisting of a ring of 5 carbon atoms and 1 oxygen atom, said cyclic ether having zero or one internal ethylenic double bond, and wherein at least one of said 5 carbon atoms of said cyclic ether is substituted with:

a. a polyolefin,
b. a short chain hydrocarbyl group of 1 to about 10 carbon atoms, or
c. the requisite number of hydrogens to complete the valence at the substituted carbon atom.

9. The compound of claim 8 wherein said polyolefin substitution of (a) is at least one carbon atom separated on the cyclic ether from the oxygen atom of the cyclic ether.

10. The compound of claim 3, wherein the polyolefin is a PIB of number average molecular weight of from about 140 to about 5000.

11. A composition comprising (A) an oil of lubricating viscosity, and (B) an ashless compound comprising the reaction product of a long chain ethylenically unsaturated hydrocarbyl group with a non-carboxy-substituted carbonyl compound selected from a aldehyde and a ketone, wherein the compound is a polyolefin substituted dihydropyran.

12. The composition of claim 11 additionally comprising (C) a dispersant comprising at least one of a carboxylic, amine, Mannich, post-treated, or polymeric dispersant.

13. The composition of claim 12, wherein the dispersant is a carboxylic dispersant.

14. The composition of claim 13, wherein said carboxylic dispersant is a PIB-succinimide.

15. The composition of claim 13, said carboxylic dispersant being present from about 0.01 to about 20 wt. % on an active basis, preferably about 0.05 to about 10 wt. %, or about 0.08 to about 5 wt. %, alternately about 0.1 to about 3 wt. %.

16. A method of operating an engine comprising (1) supplying to the engine a composition comprising (A) an oil of lubricating viscosity, and (B) an ashless compound comprising the reaction product of a long chain ethylenically unsaturated hydrocarbyl group with a non-carboxy-substituted carbonyl compound selected from an aldehyde and a ketone, wherein the compound is a polyolefin substituted dihydropyran, and (2) operating the engine.

* * * * *